United States Patent [19]
Whitehead

[11] Patent Number: 5,667,995
[45] Date of Patent: Sep. 16, 1997

[54] PROCESS FOR THE PREPARATION OF CYCLIC KETONES

[75] Inventor: Ian Michael Whitehead, Bernex, Switzerland

[73] Assignee: Firmenich SA, Geneva, Switzerland

[21] Appl. No.: 682,762

[22] PCT Filed: Dec. 12, 1994

[86] PCT No.: PCT/IB94/00409

§ 371 Date: Jul. 31, 1996

§ 102(e) Date: Jul. 31, 1996

[87] PCT Pub. No.: WO96/18742

PCT Pub. Date: Jun. 20, 1996

[51] Int. Cl.[6] .................................................. C12P 7/40
[52] U.S. Cl. ............... 435/135; 435/136; 435/142; 435/143; 435/148; 435/280; 435/830; 435/911; 560/122
[58] Field of Search .................................. 435/135, 136, 435/142, 143, 148, 830, 911, 280; 560/122

[56] References Cited

U.S. PATENT DOCUMENTS 5,168,054 12/1992 Cardillo et al. ........................ 435/125

FOREIGN PATENT DOCUMENTS

| | | |
|---|---|---|
| 0 110 142 | 10/1983 | European Pat. Off. . |
| 0 354 000 | 7/1990 | European Pat. Off. . |
| 1417723 | 10/1965 | France . |
| 216734 | 12/1984 | Germany . |
| 1286266 | 8/1972 | United Kingdom . |

OTHER PUBLICATIONS

B.A. Vick et al., "Biosynthesis of Jasmonic Acid by Several Plant Species", *Plant Physiol.* (1984) 75, 454–462.

P.A. Grieco et al., "Cycloalkenone Synthesis via Lewis Acid Catalyzed Retro Diels–Alder Reactions of Norbornene Derivsatives: Synthesis of 12–Oxophytodienoic Acid", *J. Org. Chem.* (1989) 54, 6008–6010.

*Primary Examiner*—Herbert J. Lilling
*Attorney, Agent, or Firm*—Pennie & Edmonds LLP

[57] ABSTRACT

We describe a bioorganic process for the preparation of cyclopentanone and cyclopentenone derivatives of formula

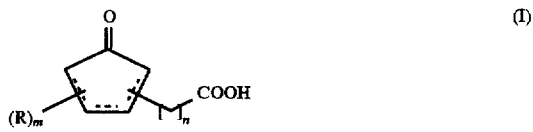

by β-oxidation of appropriate substrates, carried out by means of microorganisms.

The process is useful for preparation of 3-oxo-2-pentyl-1-cyclopentaneacetic and (Z)-3-oxo-2-(2-pentenyl)-1-cyclopentane-acetic acids and their methyl esters, compounds useful in the perfume and flavor industries.

9 Claims, No Drawings

PROCESS FOR THE PREPARATION OF CYCLIC KETONES

TECHNICAL FIELD

The present invention relates to the field of biorganic synthesis. It concerns, more particularly, a process for the preparation of cyclic ketones of formula

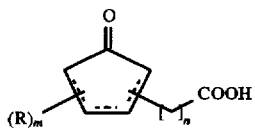
(I)

optionally having a double bond in one of the positions indicated by the dotted lines and wherein: m represents an integer from 0 to 3 and n an integer from 0 to 10; each of the symbols R, which can be identical or different, stands for hydrogen or for a saturated or unsaturated, linear or branched, alkyl radical having 1 to 6 carbon atoms; and each of the substituent groups can be located in any available position of the ring; the process being characterized in that a substrate containing one or several cyclic carboxylic derivatives of formula

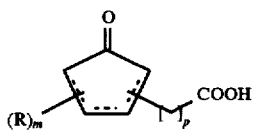
(II)

wherein the dotted lines and the symbols R and m have the meaning indicated in formula (I), p>n+2 and is defined as being an even integer when n is even and an odd number when n is odd, is added to a culture of a microorganism capable of β-oxidising the fatty acid chain of said derivatives to form at least one of the desired ketones, which is then extracted from the reaction medium.

PRIOR ART

Microbiological processes involving β-oxidation of substrates derived from fatty acids are known in the prior art. For example, U.S. Pat. No. 5,168,054 discloses a process of this type for the preparation of lactones starting from derivatives of linolenic, linoleic and oleic acids. However, to our knowledge, such processes have never been applied to cyclic carboxylic derivatives such as those presently used.

DESCRIPTION OF THE INVENTION

We have now discovered that the process according to the present invention makes it possible to prepare a great variety of cyclopentenone and cyclopentanone derivatives, in industrially applicable conditions and very advantageous yields. The process of the invention is in fact of very wide application, both as regards the nature of the substrates and the variety of microorganisms which can be used.

It has been established that one can use with equal success substrates wherein the fatty acid chain is located in the α or β position of the ring, with respect to the ketonic group, and that said ring can further carry other substituent R groups, identical to or distinct from each other.

Thus, according to a preferred and particularly advantageous embodiment of the invention, there is used a substrate of formula

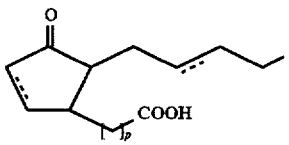
(IIa)

wherein the dotted lines indicate the location of a single or double bond and p>n+2 and is an odd number. According to this preferred embodiment, there can thus be obtained compounds of formula

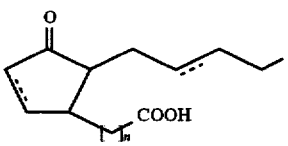
(Ia)

n being an odd integer, which compounds include cyclopentanone derivatives useful for the synthesis of fragrant molecules. For example, 3-oxo-2-(2-pentenyl)-1-cyclopentaneacetic acid, or jasmonic acid, is a precursor of methyl jasmonate, a compound much appreciated in perfumery and a natural component of jasmine essential oil.

Likewise, 3-oxo-2-pentyl-1-cyclopentaneacetic acid, or dihydrojasmonic acid, is a precursor of Hedione® (methyl 3-oxo-2-pentyl-1-cyclopentaneacetate; origin: Firmenich SA, Geneva, Switzerland), a perfuming ingredient much valued for its floral, jasmine-like fragrance and its exhalting odor effect.

In addition to their use fullness in perfumery, these acids and their methyl esters are also useful for the flavor industry, in the preparation of edible products, and there is therefore a real need for a bioorganic process allowing their preparation via a microbiological pathway.

Furthermore, it is also known that several varieties of plants are capable of producing these compounds and that jasmonic acid and methyl jasmonate in particular play an important role in the metabolism of such plants, namely as growth regulators. This has prompted the interest of several investigators to study their biosynthesis, occurring via the action of enzymes present in the corresponding vegetable tissues (see for example, B. A. Vick et al., Plant Physiol. 1984, 75, 458–61). However, it is clear that the isolation of the above-mentioned compounds from such vegetable tissues is not an economically viable synthesis on a large scale.

Now, the process according to the present invention brings precisely a novel solution to the problem of the bioorganic synthesis of these compounds. Thanks to the instant process, the compounds of formulae (I) and (Ia) can be prepared in excellent yields, by means of a large variety of microorganisms, which organisms were unknown heretofore for their capability to metabolise the formula (II) substrates, and more particularly the formula (IIa) substrates which make it possible to obtain jasmonic and dihydrojasmonic acids. Therefore, it could not have been predicted that a process such as presently claimed could open a new and general pathway for the preparation of cyclopentenone and cyclopentanone derivatives, which turns out to be particularly useful for the synthesis of ingredients of great value in the fragrance and food industries.

In addition, it has been observed that particular embodiments of the process of the invention can favor the formation of specific isomers of compounds (Ia). In fact, as a result of their structure, these compounds can assume two stereoisomeric forms of cyclanic cis or trans configuration, each of which possesses two enantiomers.

It should however be noted that, although the production of jasmonic and dihydrojasmonic acids is one of the main aims of the invention, it is nevertheless the case that the process presently disclosed is of a far more general application and allows the preparation of a large variety of cyclopentenone and cyclopentanone derivatives.

For example, according to another embodiment of the invention, there is used as substrate a compound of formula

(IIb)

wherein p has the meaning indicated in formula (II), to obtain 2-oxo-1-cyclopentaneacetic acid and higher homologues thereof.

In actual fact, there seems to be no limitation to the nature of the substrates which can be transformed according to the process above-described. Thus, one can also use substrates possessing even longer fatty acid side chains than those cited above, and such chains may optionally be unsaturated and even carry lower alkyl radicals, namely methyl and ethyl radicals, as substituents. It should be noted that, when the substrate possesses a very long fatty acid chain, the process of the invention makes it possible to convert it into several lower homologues, which are formed in sequential reactions and which can then themselves be converted into lower homologues, until formation of the corresponding compounds (I) having n=0 or 1. In this manner, the oxidation product can be formed of one or several such metabolites from the reaction sequence, depending on the reaction time and on the kinetic characteristics of the successive β-oxidations. If desired, once the reaction mixture has been extracted from the medium, the various components of this mixture can be separated via the usual methods, such as chromatography or distillation. Alternatively, and according to the nature of the product that is desired to obtain, the microorganism is allowed to act until all the intermediate metabolites have been converted at once, to collect essentially only the last product of the reaction sequence.

In this way, one can for instance obtain essentially jasmonic acid, or 2-(2-pentenyl)-3-oxo-1-cyclopentaneacetic acid, starting from 3-oxo-2-[2-pentenyl]-1-cyclopentaneoctanoic acid, a natural component of certain plants, or yet starting from one of its lower homologues. Such conversions are described in detail in the examples presented further on.

Amongst the microorganisms that can be used according to the invention to carry out the β-oxidation of substrates (II), those of the Saccharomyces or Rhodococcus genus turned out to be particularly advantageous, namely for the preparation of jasmonic and dihydrojasmonic acids.

As preferred microorganisms to be used according to the invention, there can be further cited those selected from the group consisting of *Rhodococcus rhodochorus, Rhodococcus erytropolis, Rhodococcus sp., Nocardia calcarea, Arthrobacter petroleophagus, Arthrobacter artrocyanus, Arthrobacter ureafaciens, Aspergillus niger, Saccharomyces cerivisae, Mycobacterium phlei, Streptomyces viridosporus, Streptomyces rosechromogenus, Streptomyces bacilliaris, Cylindrocarpon candidum, Escherichia coli, Hansenula polyrmorpha, Pseudomonas Sp., Serratia marcesens* et *Aspergillus oryzae*. Such microorganisms can be obtained from Internationally recognized deposit authorities. In the particular case of Saccharomyces, they can be bought from specialized firms, which frequently provide locally cultured strains, stemming from the beer, wine or baking industries. All these species are quite convenient for the process according to the invention. Cultures of these microorganisms are obtained in the conventional manner. Their prior growth is carried out in current nutritive mediae and under the usual conditions, either in stationary phase or under stirring.

The cells are then isolated from the culture medium, for example by centrifuging, and suspended in an aqueous medium containing the above-mentioned substrates and generally devoid of any other nutritive or metabolisable source, at temperatures preferably comprised between 20° and 35° C., for variable but relatively short periods of times, typically comprised between 24 and 72 hours, under aerobic conditions. During the reaction, the pH of the medium will be preferably maintained between 5 and 10.

According to a particular embodiment of the invention, before adding the substrate to the microorganism culture, there is provided a first step of preparation via aeration of the culture for a period of time, which step consists in suspending said culture in water, under aerobic conditions and stirring, at a temperature comprised between 15° and 30° C., for an amount of time sufficient to ensure that any nutritive source, of endogenous or exogenous origin, has been entirely consumed before addition of the substrates of formula (II). Such a preparation step is particularly appropriate whenever the microorganism culture, as a result of its growth conditions, possesses a residual nutritive source, namely a carbohydrate source, as is typically the case of Saccharomyces for example.

The substrate is then added to the microorganism culture thus prepared, such addition being preferably carried out in the absence of any other nutritive source, under the conditions cited above.

The cells are then separated from the reaction medium by centrifugation or ultrafiltration and the aqueous solution thus obtained acidified and repeatedly extracted by means of an appropriate solvent, e.g. diethyl ether. The combined organic layers are then treated in the usual manner and, if desired, their components (I) separated by chromatography.

It should be noted that the acids thus obtained can then be readily esterified by chemical or enzymatic means to form the corresponding esters.

The substrates of formula (II) are either commercial origin compounds or can be easily prepared from commercial products. For example, the substrates derived from cyclopentanone can be conventionally prepared via addition reactions on cyclopent-2-en-1-one, or derivatives thereof, according to the following general scheme:

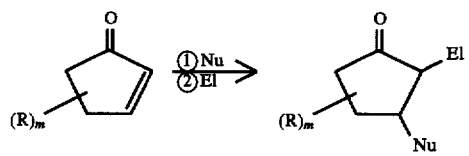

R and m defined in Formula (I)
El - electrophile group
Nu - nucleophile group the fatty acid chain being introduced in the form of a group acting as an electrophile or as a nucleophile, depending on the ring position into which one wishes to introduce it and on the conditions of the addition reaction. For example, the formula (IIa) substrates having a saturated ring can be prepared following the scheme hereinafter:

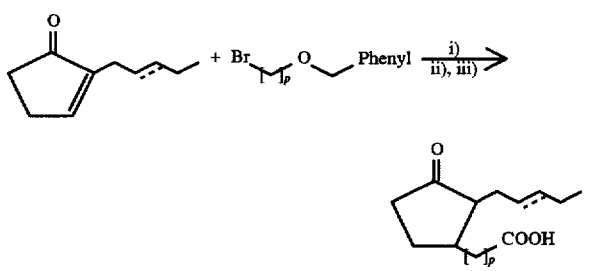

i) Mg, (C₂H₅)₂O, CuBr.(CH₃)₂S, −40° C.
ii) (CH₃)₃SiI, CH₂Cl₂, r.t., aq. HCl, THF, R.t.
iii) aq. H₂CrO₄, H₂SO₄, acetone, r.t.

In this scheme, the dotted line and p have the meaning indicated in formula (IIa). The starting cyclopentenone is a known compound (see, for example, EP 110 142) and the brominated reagent can be obtained in conventional manner and as described further on, starting from commercial origin diols.

As regards the formula (II) substrates which possess an endocylic double bond, they can be obtained in analogous manner to that described for example by P. A. Grieco et al. in J. Org. Chem. 1989, 54, 6008–6010, and as represented hereinafter:

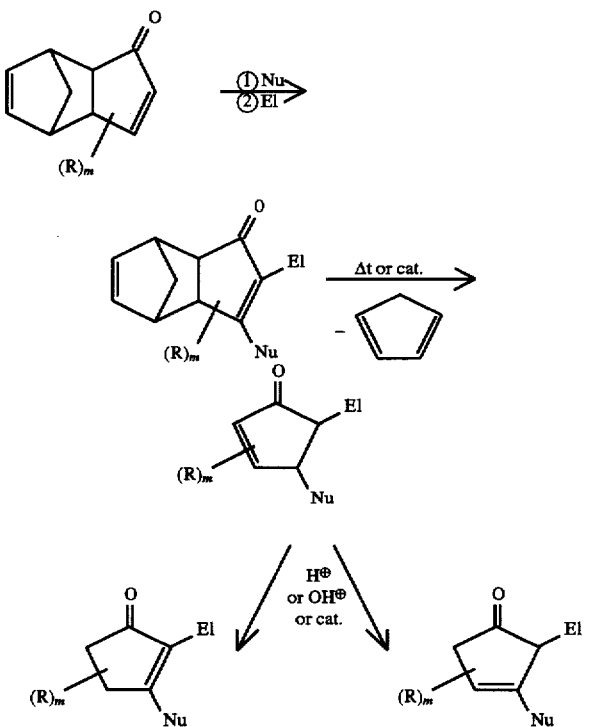

R and m defined in formula (I)
El - electrophile group
Nu - nucleophile group

The conditions of these conventional reactions are described in detail in the examples presented further on.

Clearly, the substrates of formula (II) can be used in the form of racemic mixtures of cis and trans configuration stereoisomers, as cis and trans configuration racemates, or yet in the form of any one of the four possible diastereomers in pure state. It was observed that certain microrganisms, when put into contact with racemic substrates, containing mixtures of cis and trans isomers, favored the formation of particular chiral final products. The details of such transformations are presented in the following examples.

The process of the invention will now be described in further detail by way of the following examples, wherein the temperatures are indicated in degrees centigrade and the abbreviations have the ususal meaning in the art. In the Tables, the cited amounts of the products obtained are indicated in percentage, relative to an internal standard and as measured by chromatographic analysis.

EMBODIMENTS OF THE INVENTION

EXAMPLE 1

General Method I

A 5 neck flask (200 ml), fitted with a Medimix® type turbine, a pH measuring cell, an air inlet, a condenser and a sampling outlet, was charged with the microorganism culture (10 g of wet biomass) and 50 ml of demineralised water. The cell suspension was aerated (1 v/v/m) and stirred (1,000 rpm) overnight at 30°. The suspension pH was then adjusted to 5.5 and a solution of the substrate to be used, in the present case 3-oxo-2-pentyl-1-cyclopentaneoctanoic acid (100 mg, 0.34 mmole, 2 g/l; see preparation further on), in water (10 ml) was added thereto. The reaction was followed by taking aliquots (1 ml) of the mixture at regular intervals. Such samples were centrifuged in plastic tubes of the Eppendorf type during 2 minutes to precipitate the cells. An aliquot (0.45 ml) of the supernatant transparent solution was then acidified with HCl 5M (0.05–0.1 ml) and extracted with diethyl ether (2 times, identical volumes). The organic extracts were combined, dried under nitrogen and treated with diazomethane to form the methyl esters of the acids contained in the reaction product. This mixture of esters was then analysed by gas chromatography. After a 24 h reaction, the reaction mixture was centrifuged (20 min, at 10,000 rpm) to precipitate the cells and the supernatant liquid was decanted. In order to wash the cells, the latter were once again suspended in 50 ml of water and stirred for 30 min. After recentrifuging, there was obtained a second supernatant liquid which was combined with the first and the pH of which was adjusted to 12 with NaOH (10%). The resulting solution was extracted with diethyl ether (3 times, identical volumes) to separate the neutral fraction. The pH was then adjusted to 2 with HCl (5M) and the acidic fraction collected by extraction. The combined organic extracts were dried over Na₂SO₄ and the solvent stripped under vacuum. An aliquot was then methylated by means of diazomethane and the product thus obtained analysed by gas chromatography [SPB5 type column, 30 m length, 0.32 mm internal diameter, 50°(0')–230°(5') at 10°/min; sample dissolved in 0.1 ml of diisopropylether containing 1 g/l of methyl myristate as internal standard—retention time 13.91 minutes].

Upon a test carried out on a scale 5 times larger, using *Saccharomyces cerevisiae* (origin: Here, Schweiz, AG, 9507 Stettfurt, Switzerland), the following compounds were isolated and identified [GC-MS: M/Z (% relative to the internal standard)]:

1. methyl 3-oxo-2-pentyl-1-cyclopentaneacetate trans isomer: retention time—13.18 min
   GC-MS: 226 (3) [M⁺], 195 (2) [M—OCH₃⁺], 156 (35) [M—C₅H₁₁+H⁺], 153 (31) [M—CH₂—COOCH₃⁺], 109 (5), 96 (10), 83 (100) [C₅H₆O+H⁺], 82 (24) [C₅H₆O⁺], 55(13)

cis isomer: retention time—13.46 min
   GC-MS: 226 (5) [M⁺], 156 (25) [M—C₅H₁₁+H⁺], 153 (29) [M—CH₂COOCH₃⁺], 109 (5), 103 (15), 96 (11), 83 (100) [C₅H₆O+H⁺], 82 (24) [C₅H₆O⁺], 55 (19)

2. methyl 3-oxo-2-pentyl-1-cyclopentanebutanoate trans isomer: retention time—15.53 min
GC-MS: 254 (1) [M$^+$], 184 (13) [M—C$_5$H$_{11}$+H$^+$], 153 (29) [M—(CH$_2$)$_3$COOCH$_3$$^+$], 109 (4), 97 (5), 83 (100) [C$_5$H$_6$O+H$^+$], 82 (30) [C$_5$H$_6$O$^+$], 55 (10)

cis isomer: retention time—15.72 min
GC-MS: 254 (1) [M$^+$], 184 (13) [M—C$_5$H$_{11}$+H$^+$], 153 (29) [M—(CH$_2$)$_3$COOCH$_3$$^+$], 109 (4), 97 (5), 83 (100) [C$_5$H$_6$O+H$^+$], 82 (29) [C$_5$H$_6$O$^+$], 55 (10)

3. methyl 3-oxo-2-pentyl-1-cyclopentanehexanoate trans isomer: retention time—17.42 min
GC-MS: 282 (1) [M$^+$], 251 (4) [M—OCH$_3$$^+$], 212 (13) [M—C$_5$H$_{11}$+H$^+$], 153 (18) [M—(CH$_2$)$_5$COOCH$_3$$^+$], 130 (29), 83 (100) [C$_5$H$_6$O+H$^+$], 82 (8) [C$_5$H$_6$O$^+$], 55 (11)

cis isomer: retention time—17.65 min 4. methyl 3-oxo-2-pentyl-1-cyclopentaneoctanoate trans isomer: retention time—19.35 min
GC-MS: 310 (1) [M$^+$], 279 (2) [M—OCH$_3$$^+$], 240 (11) [M—C$_5$H$_{11}$+H$^+$], 153 (31) [M—(CH$_2$)$_7$COOCH$_3$$^+$], 83 (100) [C$_5$H$_6$O+H$^+$], 82 (38) [C$_5$H$_6$O$^+$], 55 (10)

Preparation of the Starting Product

The starting product in the above-described reaction, i.e. 3-oxo-2-pentyl-1-cyclopentaneoctanoic acid, was prepared as follows. A solution of 1,8-octanediol (15 g, 0.1 mole) in toluene (235 ml) and THF (tetrahydrofuran, 15 ml) was added dropwise to a NaH slurry (oil dispersion 65–70%, 5.3 g, 0.15 mole) in toluene (50 ml), kept under stirring and N$_2$, at room temperature. The mixture was heated to reflux during 60 h and benzyl chloride (33 g, 0.26 mole) was then added and the mixture kept at reflux for yet 60 h. The cooled reaction mixture was poured on cold sat. aq. NH$_4$Cl and extracted with ether. The combined organic phases were washed with aq. sat. NaCl, dried over anhydrous Na$_2$SO$_4$ and concentrated under vacuum to provide a pale yellow oil (24.5 g). After chromatography on silica column (350 g), with cyclohexane/ethyl acetate 4:1 as eluting agent, followed by bulb-to-bulb distillation under vacuum, pure 8-benzyloxyoctan-1-ol was obtained, in the form of a pale yellow oil (11.9 g, yield 49%).

B.p.: 200°–220° (bath)/4 Pa Rf (cyclohexane/ethyl acetate 7:3) 0.36 IR (CDCl$_3$): 3450 (broad), 3010, 2934, 2858, 1454, 1095 cm$^{-1}$ NMR ($^1$H, 360 MHz, D$_2$O): 1.25–1.45 (8H); 1.45–1.70(4H); 3.46(t, J=7 Hz, 2H); 3.60(t, J=7 Hz, 2H); 4.50(s, 2H); 7.23–7.38(5H) δ ppm NMR ($^{13}$C): 138.6 (s); 128.3(d); 127.6(d); 127.5(d); 72.9(t); 70.5(t); 62.9(t); 32.7(t); 29.7(t); 29.4(2t); 28.1(t); 25.7(t) δ ppm MS: 236 (2, M$^+$), 107(59), 91(100)

To a stirred solution of this compound (11.6 g, 0.049 mole) and pyridine (9.8 g, 0.12 mole) in CH$_2$Cl$_2$ (100 ml), there was added by portions, at room temperature (r.t.) and under N$_2$, tosyl chloride (12.8 g, 0.067 mole). After 20 h at r.t., the mixture was poured on 5% aq. HCl, cooled and extracted (CH$_2$Cl$_2$). The organic phase was washed with sat. aq. NaHCO$_3$ and brine, dried over anhydrous Na$_2$SO$_4$ and concentrated. The semi-crystalline residual oil (19.2 g; raw tosylate of the above-mentioned benzyloxyoctanol) was retaken in acetone (400 ml) and LiBr (10.9 g, 0.126 mole) added thereto. The stirred mixture was then taken to reflux during 90 min, cooled to r.t. and filtered. The filtrate was concentrated and dissolved in ether (150 ml). This organic phase was then successively washed with H$_2$O and aq. sat. NaCl and dried over anhydrous Na$_2$SO$_4$. Concentration under vacuum (80°/8 Pa) provided 1-benzyloxy-8-bromooctane in the form of a pale yellow oil (12.4 g; yield 84%).

IR (CHCl$_3$): 3011, 2934, 2858, 1454, 1364, 1098 cm$^{-1}$ NMR ($^1$H, 360 MHz): 1.25–1.50(8H); 1.60(m, 2H); 1.83(m, 2H); 3.39(t, J=7 Hz, 2H); 3.46(t, J=7 Hz, 2H); 4.50(s, 2H); 7.22–7.37(5H) δ ppm NMR ($^{13}$C): 138.7(s); 128.3(d); 127.6 (d); 127.5(d); 72.9(t); 70.4(t); 33.9(t); 32.8(t); 29.7(t); 29.3 (t); 28.7(t); 28.1(t); 26.1(t) δ ppm MS: 298 (11, M$^+$), 207(52), 188(17), 147(16), 109(22), 9(100)

A solution of this bromooctane (11 g, 0.037 mole) in ether (36 ml) was added dropwise to a stirred slurry of Mg turnings (0.91 g, 0.037 mole) in ether (4 ml), at r.t. and under N$_2$. The resulting Grignard reagent was heated to reflux for 30 min, then cooled and added dropwise to a slurry of CuBr.(CH$_3$)$_2$S (3.2 g, 0.015 mole) in ether (30 ml), under stirring and at –44°. After 3 min, a solution of 2-pentylcyclopent-2-en-1-one (4.7 g, 0.028 mole; see EP 110 142, for example) in ether (15 ml) was added dropwise during 30 min, at –44°. After an additional 15 min at –40°, the mixture was allowed to attain 0° during 1 h and then poured over cold aq. NH$_4$Cl. Extraction with ether afforded an organic phase which was successively washed with H$_2$O and sat. aq. NaCl and dried over anhydrous Na$_2$SO$_4$. Concentration under vacuum afforded a semi-crystalline green oil (12.7 g) which was purified by chromatography [SiO$_2$ (280 g) ; eluting agent: cyclohexane/ethyl acetate 19:1)] to afford 3-(8'-benzyloxyoct- 1'-yl)-2-pentylcyclopentan-1-one (12:1 trans/cis mixture) in the form of a pale yellow oil (3.1 g; yield 30%), which was dried at 100°/7.9 Pa.

R$_f$(cyclohexane/ethyl acetate 9:1) 0.43 IR (CHCl$_3$): 3011, 2930, 2857, 1732, 1455, 1098 cm$^{-1}$ NMR ($^1$H, 360 MHz): 0.88(t, J=7 Hz, 3H); 1.20–2.40(28H); 3.47(t, J=7 Hz, 2H); 4.50(s, 2H); 7.23–7.37(5H) δ ppm NMR ($^{13}$C): 221.5(s); 138.7(s); 128.3(d); 127.6(d); 127.5(d); 72.9(t); 70.5(t); 55.1 (d); 41.6(d); 37.9(t); 34.8(t); 32.2(t); 29.8(t); 29.6(t); 29.5(t); 28.1(t); 27.1(t); 26.6(t); 26.2(t); 22.5(t); 14.1(q) δ ppm MS: 372 (6, M$^+$), 243(6), 196(8), 173(14), 153(35), 91(100), 83(92)

A solution of this cyclopentanone (3 g, 8.05 mmole; trans/cis 12:1) in ethanol (30 ml) containing 10% Pd—C (0.24 g), was hydrogenolysed at r.t. during 4 h. After filtration (Hyflo®), concentration under vacuum and bulb-to-bulb distillation, 3-(8'-hydroxy-1'-octyl)-2-pentylcyclopentan-1-one was obtained (12:1 trans/cis mixture) in the form of a pale yellow oil (2.1 g; yield 92%).

B.p.: 230°–240° (bath)/5.3 Pa IR (CHCl$_3$): 3437 (broad), 2930, 2857, 1732, 1456, 1160, 1051 cm$^{-1}$ NMR ($^1$H, 360 MHz, D$_2$O): 0.88(t, 3H); 1.20–2.00(24H); 2.00–2.36(4H); 3.65(t, J=7 Hz, 2H) δ ppm NMR ($^{13}$C): 221.6(s); 63.0(t); 53.1(d); 41.6(d); 37.9(t); 34.8(t); 32.8(t); 32.2(t); 29.8(t); 29.6(t); 29.4(t); 28.1(t); 27.1(2t); 26.6(t); 25.8(t); 22.5(t); 14.1(q) δ ppm MS: 282 (0, M$^+$), 212(4), 153(17), 83(100)

Jones reagent (H$_2$CrO$_4$/aq. H$_2$SO$_4$; 7.2 ml of a 2.5M solution) was added dropwise to a stirred solution of the latter cyclopentanone (2 g, 7.1 mmole; trans/cis 12:1) in acetone (40 ml) at 20°, under N$_2$. After a further 40 min at 22°–24°, the mixture was poured into water and extracted with ether. The organic phase was successively washed with H$_2$O, 10% aq. NaCl and sat. aq. NH$_4$Cl, dried over anhydrous Na$_2$SO$_4$ and concentrated under vacuum. The resulting yellow oil (2.1 g) was purified by chromatogarphy [SiO$_2$ (100 g); eluting agent:cyclohexane/ethyl acetate 1:1.5)] to afford the desired 3-oxo-2-pentyl-1-cyclopentaneoctanoic acid (trans/cis 12:1) as a viscous pale yellow oil (1.9 g; yield 90%).

IR (CHCl$_3$): 3050 (broad), 2931, 2858, 1732, 1710, 1460, 1160 cm$^{-1}$ NMR ($^1$H, 360 MHz, D$_2$O): 0.89(t, J=7 Hz, 3H); 1.20–2.35(28H); 2.37(t, J=7 Hz, 2H) δ ppm NMR ($^{13}$C):

221.8(s); 179.6(s); 55.1(d); 41.6(d); 37.9(t); 34.8(t); 34.0(t); 32.2(t); 29.6(t); 29.2(t); 29.0(t); 28.1(2t); 27.1(t); 26.6(t); 24.7(t); 22.5(t); 14.1(q) δ ppm MS: 297 (2, M$^+$), 279(3), 226(9), 153(17), 83(100)

EXAMPLE 2

We proceeded according to the general method I described in Example 1, using a variety of different microorganisms, cited in the table below. In this table, the compounds are indicated by the number attributed to them in Example 1. These results relate to the product obtained after 24 h of reaction, i.e. of activity of the corresponding microorganism. The yield in compound 1 represents the molar % relative to compound 4, based on the amount of the corresponding starting acid (100 mg).

TABLE I

| Microorganism | Weight of acid extract (mg) | Compound (% GC) 1 | 2 | 3 | 4 | Yield in compound 1 (molar %) |
|---|---|---|---|---|---|---|
| Serratia marcesens ATCC 8100 | 36.6 | 84.5 | 11.9 | 1.4 | 2.2 | 43.2 |
| Aspergillus niger ATCC 16888 | 25.0 | 74.4 | 9.8 | 6.0 | 9.8 | 26.0 |
| Escherichia coli ATCC 8677 | 35.8 | 49.0 | 23.2 | 4.8 | 23.1 | 35.8 |
| Saccharomyces cerevisiae | 35.7 | 31.8 | 54.0 | 9.1 | 5.0 | 15.9 |
| Streptomyces viriosporus ATCC 39115 | 34.3 | 30.4 | 25.9 | 8.4 | 35.3 | 14.6 |
| Hansenula polymorpha | — | 13.0 | 52.7 | 8.7 | 25.5 | — |
| Pseudomonas Sp. DMS 1650 | — | 0.0 | 2.4 | 2.5 | 95.1 | — |

This table shows that all the microorganisms were able to carry out the β-oxidation of the 3-oxo-2-pentyl-1-cyclopentaneoctanoic, -hexanoic and -butanoic acids. The yields in final acid, i.e. 3-oxo-2-pentyl-1-cyclopentaneacetic acid, and thus in the corresponding compound 1, can of course be distinctly improved by prolonging the reaction beyond 24 h. Furthermore, the described extraction procedure may also be improved to minimize the losses in the desired products.

EXAMPLE 3

General Method II

The microorganism to be used was prior grown on a starch-containing medium for three days. At the end of the three days, all the starch had been consumed. The cells were collected by centrifugation and a portion of the resulting biomass (2 g), as well as 8 ml of demineralized water, were placed in an Erlenmeyer type flask (50 ml) containing the substrate to be used, in the present case (Z)-3-oxo-2-(2-pentenyl)-1-cyclopentaneoctanoic acid (20 mg, 2 g/l; see preparation further on). The vial was sealed with a cotton wool bung and placed on an orbital shaker for 24 h, at 30° and 140 rpm. The cells were then spun down by centrifugation (10,000 rpm) for 15 min at r.t. After removing the supernatant with a pipette, the cells were resuspended in demineralized water (10 ml) and then spun down again as above. The resulting supernatant was combined with that first obtained as above-described and the combined volume adjusted to 25 ml with de-ionized water. This solution was then brought to pH 2 with H$_2$SO$_4$ (10%) and extracted with diethyl ether (1×50 ml et 1×25 ml). The combined organic phases were dried over anhydrous MgSO$_4$. The solvent was stripped under nitrogen flow and the product weighed. It was then treated with diazomethane to afford the corresponding methyl esters. The product thus obtained was anlyzed by chromatography, relative to an external standard. To this end, a solution in 1 ml of methyl pentadecanoate (5 g/l) was prepared and chromatographed [SPB5 column, 30 m length, 0.32 mm internal diameter, 80°(0')–230°(20') at 15°/min]. The amount of each of the components was assessed on the basis of the area of the corresponding peak, relative to that of the standard. Proceeding as described above, upon a reaction carried out with *Saccharomyces cerevisiae* (origin: Switzerland), the following products were obtained and identified.

A. methyl (Z)-3-oxo-2-(2-pentenyl)-1-cyclopentaneacetate trans isomer: retention time—10.28 min
GC-MS: 224 (31) [M$^+$], 206 (4) [M—H$_2$O$^+$], 193 (10) [M—OCH$_3^+$], 177 (6), 156 (23) [M—C$_5$H$_9$+H$^+$], 151 (31) [M—CH$_2$COOCH$_3$+], 109 (24), 95 (30),83 (100)[C$_5$H$_6$O+H$^+$], 55 (37), 41 (73)

cis isomer: retention time—10.56 min
GC-MS: 224 (24) [M$^+$], 206 (12) [M—H$_2$O$^+$], 177 (13), 156 (15) [M—C$_5$H$_9$+H$^+$], 151 (31) [M—CH$_2$COOCH$_3^+$], 109(23), 95 (42), 83 (100) [C$_5$H$_6$O+H$^+$], 55 (19), 41 (81)

B. methyl (Z)-3-oxo-2-(2-pentenyl)-1-cyclopentanebutanoate trans isomer: retention time—12.74 min
GC-MS: 252 (17) [M$^+$], 234 (7) [M—H$_2$O$^+$], 184 (10) [M—C$_5$H$_9$+H$^+$], 151 (59) [M—(CH$_2$)$_3$COOH$_3^+$], 109 (22), 95 (35), 83 (100) [C$_5$H$_6$O+H$^+$], 41 (67)

cis isomer: retention time—13.10 min
GC-MS: 252 (8) [M$^+$], 234 (20) [M—H$_2$O$^+$], 205 (10), 184 (9) [M—C$_5$H$_9$+H$^+$], 151 (37) [M—(CH$_2$)$_3$COOH$_3^+$], 109 (30), 95 (47), 83 (100) [C$_5$H$_6$O+H$^+$], 41 (73)

C. methyl (Z)-3-oxo-2-(2-pentenyl)-1-cyclopentanehexanoate trans isomer: retention time—16.37 min
GC-MS: 280 (7) [M$^+$], 262 (8) [M—H$_2$O+], 212 (16) [M—C$_5$H$_9$+H$^+$], 151 (39) [M—(CH$_2$)$_5$COOCH$_3^+$], 95 (40), 83 (100) [C$_5$H$_6$O+H$^+$], 82 (8) [C$_5$H$_6$O$^+$], 41 (55)

cis isomer: retention time—17.10 min

D. methyl (Z)-3-oxo-2-(2-penténtyl)-1-cyclopentaneoctanoate trans isomer: retention time—22.71 min
GC-MS: 308 (4) [M$^+$], 290 (4) [M—H$_2$O$^+$], 277 (7) [M—OCH$_3^+$], 240 (18) [M—C$_5$H$_9$+H$^+$], 151 (43) [M—(CH$_2$)$_7$COOCH$_3^+$], 124 (35), 95 (48), 83 (100) [C$_5$H$_6$O+H$^+$], 55 (43)

cis isomer: retention time—23.82 min
GC-MS: 308 (3) [M$^+$], 290 (4) [M—H$_2$O$^+$], 277 (5) [M—OCH$_3^+$], 240 (14) [M—C$_5$H$_9$+H$^+$], 151 (37) [M—(CH$_2$)$_7$COOCH$_3^+$], 124 (40), 95 (50), 83 (100) [C$_5$H$_6$O+H$^+$], 55 (24)

The reaction product was also analyzed on a chiral column of the Megadex® dimethylpentyl-β-cyclodextrine type (10 m×2.5 mm×0.25 μm film thickness) using a temperature program of 50°(1')–130°(15'), heating 15°/min, and up to 220°(5'), heating 2°/min. The retention times of each of the chiral species corresponding to each of compounds A, B, C and D above are indicated in the following table.

TABLE II

| Chiral isomer | Retention time (min) |
|---|---|
| (−)-trans-A | 17.61 |
| (+)-trans-A | 18.93 |
| (+)-cis-A | 20.29 |
| (−)-cis-A | 20.29 |
| (−)-trans-B | 33.78 |
| (+)-trans-B | 34.83 |
| (+)-cis-B | 35.86 |
| (−)-cis-B | 35.86 |
| (−)-trans-C | 44.57 |
| (+)-trans-C | 45.16 |
| (+)-cis-C | 46.32 |
| (−)-cis-C | 46.32 |
| (−)-trans-D | 53.7–54.1 |
| (+)-trans-D | 53.7–54.1 |
| (+)-cis-D | 55.21 |
| (−)-cis-D | 55.21 |

Preparation of the Starting Product

The starting product in the reaction described above, i.e. (Z)-3-oxo-2-(2-pentenyl)-1-cyclopentaneoctanoic acid, was prepared as follows. A solution of 1-benzyloxy-8-bromooctane (5 g, 0.015 mole; see Example 1) in ether (15 ml) was added dropwise to a stirred suspension of Mg turnings (0.38 g, 0.016 mole) in ether (2 ml), at r.t. under $N_2$. The resulting Grignard reagent was heated to reflux for a further 30 min, then cooled and added dropwise to a slurry of CuBr.$(CH_3)_2$S (1.25 g, 6 mmole) and LiBr (1.9 g, 0.022 mole) in THF (15 ml), under stirring and at −44°. After 3 min, a solution of (Z)-2-(2-pentenyl)-cyclopent-2-en-11-one (1.65 g, 0.011 mole; see, for example, F. Näf et al., Helv. Chim. Acta 1978, 2524) and trimethylsilyl chloride (2.8 ml, 0.022 mole) in ether (15 ml) was added dropwise during 30 min, at −44°. After an additional 15 min at −40°, the mixture was allowed to attain 0° during 1 h and then poured into cold aq. $NH_4Cl$. Extraction with ether afforded an organic phase which was successively washed with $H_2O$ and sat. aq. NaCl and dried over anhydrous $Na_2SO_4$. Concentration under vacuum afforded a raw oil (7 g) consisting of the trimethylsilyl enol ether of the desired intermediate, which oil was dissolved in THF (25 ml) and stirred with 10% aq. HCl (1 ml) during 30 min. After a further extraction with ether, treatment and purification by chromatography [$SiO_2$ (100 g); eluting agent:cyclohexane/ethyl acetate 19:1)] afforded (Z)-3-(8'-benzyloxyoct-1'-yl)-2-(2-pentenyl)-cyclopentan-1-one (13:1 trans/cis mixture) in the form of a viscous yellow oil (3.1 g; yield 30%), which was dried at 50°/1.3 Pa.

NMR ($^1$H, 360 MHz): 4.96(t, J=7 Hz, 3H); 1.20–2.40 (24H); 7.47(t, J=7 Hz, 2H); 4.50(s, 2H); 5.25(m, 1H); 5.42(m, 1H); 7.25–7.35(5H) δ ppm NMR ($^{13}$C): 220.8(s); 138.7(s); 133.4(d); 128.3(d); 127.6(d); 127.5(d); 125.5(d); 72.9(t); 70.5(t); 55.1(d); 41.2(d); 38.1(t); 34.7(t); 29.8(t); 29.5(2t); 27.1(t); 26.2(t); 25.4(t); 20.6(t); 14.2(q) δ ppm MS: 370 (1, M$^+$), 302(10), 279(26), 261(9), 173(10), 151(30), 91(100), 83(25)

Trimethylsilyl iodide was added via a syringe to a stirred solution of this pentanone (2.1 g, 5.7 mmole; trans/cis 13:1) in $CH_2Cl_2$ (8 ml), at r.t. and under $N_2$. After 25 min, the mixture was poured into 10% aq. $NaHSO_3$ (50 ml) and extracted with ether. The organic phase was washed successively with sat. aq. $NaHCO_3$ and sat. aq. NaCl and dried over anhydrous $Na_2SO_4$. Concentration under vacuum afforded the trimethyl silyl ether of the desired intermediate, which was dissolved in THF (15 ml) and stirred with aq. 10% HCl during 20 min. Re-extraction with ether, treatment and chromatography [$SiO_2$ (100 g); eluting agent: cyclohexane/ethyl acetate 4:1], followed by bulb-to-bulb distillation, afforded (Z)-3-(8'-hydroxyoct-1'-yl)-2-(2-pentenyl)-1-cyclopentanone (trans/cis 13:1) in the form of a colorless oil (1.25 g; yield 78%).

B.p.: 220°–240° (bath)/5.3 Pa IR ($CHCl_3$): 3440 (broad), 3015, 2930, 2857, 1732, 1462 cm$^{-1}$ NMR ($^1$H, 360 MHz, $D_2O$): 4.96(t, J=7 Hz, 3H); 1.20–2.40(24H); 3.63(t, J=7 Hz, 2H); 5.25 (m, 1H); 5.42(m, 1H) δ ppm NMR ($^{13}$C) 221.0(s); 133.5(d); 125.5(d); 62.8(t); 55.1(d); 41.1(d); 38.1(t); 34.7(t); 32.7(t); 29.8(t); 29.6(t); 29.4(t); 27.1(2t); 25.8(t); 25.4(t); 20.6(t); 14.2(q) δ ppm MS: 280 (2, M$^+$), 212(13), 151(36), 124(33), 109(15), 95(40), 83(100)

Jones reagent ($H_2CrO_4$/aq. $H_2SO_4$; 4 ml of a solution 2.5M) was added dropwise to a stirred solution of the latter cyclopentanone (1.1 g, 3.9 mmole; trans/cis 13:1) in acetone (20 ml) at 20°, under $N_2$. After a further 40 min at 22°–24°, the mixture was poured into water and extracted with ether. The organic phase was successively washed with $H_2O$, 10% aq. NaCl and sat. aq. $NH_4Cl$, dried over anhydrous $Na_2SO_4$ and concentrated under vacuum. The resulting yellow oil (2.1 g) was purified by chromatography [$SiO_2$ (50 g); eluting agent:cyclohexane/ethyl acetate 1:1.5)] to afford the desired (Z)-3-oxo-2-(2-pentenyl)-1-cyclopentaneoctanoic acid (trans/cis 13:1) in the form of a viscous pale yellow oil (1 g; yield 87%).

IR ($CHCl_3$): 3300 (broad), 3020, 2931, 1732, 1710 cm$^{-1}$ NMR ($^1$H, 360 MHz, $D_2O$): 0.96(t, J=7 Hz, 3H); 1.20–2.40 (24H); 5.24(m, 1H); 5.42(m, 1H) δ ppm NMR ($^{13}$C): 221.1(s); 179.3(s); 133.5(d); 125.5(d); 55.1(d); 41.1(d); 38.1 (t); 34.7(t); 33.9(t); 29.6(t); 29.2(t); 29.0(t); 27.1(t); 27.0(t); 25.4(t); 24.7(t); 20.6(t); 14.2(q) δ ppm MS: 294 (<0.5, M$^+$), 226(1), 151(8), 124(16), 95(26), 83(100)

EXAMPLE 4

We proceeded according to general method II described in Example 3, using the microorganisms cited in the following table. In this table, compounds A, B, C and D are the same as cited in Example 3. The results indicated relate to the product obtained after 24 h reaction. The molar yields are indicated in % relative to the added starting acid, i.e. (Z)-3-oxo-2-(2-pentenyl)-1-cyclopentaneoctanoic acid (trans/cis 13:1, 20 mg, ~65 μmole).

The results in this table show that in the case of the reactions carried out with *Rhodococcus rhodochorus*, *Arthrobacter petroleophagus* and *Aspergillus niger*, pratically no kinetic resolution between the (+) and (−) enantiomers of the substrate is observed, whereas in all other cases the amount of (+)-trans,(Z)-3-oxo-2-(2-pentenyl)-1-cyclopentaneacetic acid formed (corresponding to compound A) is larger than that of its (−)-trans enantiomer. This therefore indicates that the corresponding microorganisms are capable of kinetic resolution among the substrate enantiomers. Furthermore, it is apparent from this table that the resolution takes place essentially at the stage of the conversion of (Z)-3-oxo-2-(2-pentenyl)-1-cyclopentanebutanoic acid (corresponding to compound B) into (Z)-3-oxo-2-(2-pentenyl)-1-cyclopentaneacetic acid. The results of identical experiments carried out by way of *Cylindrocarpon candidum* CBS 132.25, *Arthrobacter atrocyanus* DSN 20127, *Streptomyces bacilliaris* DMS 40598, *Arthrobacter ureafaciens* DMS 419 or *Streptomyces rosechromogenus* seem to indicate that these microorganisms require reaction times above 24 h to carry out the β-oxidation of the substrates cited in the table, under the described reaction conditions.

TABLE III

| Microorganism | Final pH | Weight of extract (mg) | Acid fraction - Molar yield (%) | D (trans+cis) | C (trans+cis) | B (trans+cis) | A (trans+cis) | Total acids (%) | trans-A/A | Trans-D (+ and -) | Cis-D (+ and -) | Trans-C (+ and -) | Cis-C (+ and -) | (-)-trans-C/(+)-trans-C Enant. ratio | Trans-B (+ and -) | Cis-B (+ and -) | (-)-trans-B/(+)-trans-B Enant. ratio | Trans-A (+ and -) | trans-A Enant. ratio | Cis-A (+ and -) |
|---|---|---|---|---|---|---|---|---|---|---|---|---|---|---|---|---|---|---|---|---|
| Rhodococcus rhodochorus ATCC 4273 | 7.52 | 28.2 | 74.01 | 0.00 | 0.56 | 5.60 | 67.86 | 91.69 | | | | | | | 93.1 | 6.9 | | 93.9 | 0.97 | 6.1 |
| Nocardia calcarea DSM 43188 | 8.01 | 30.0 | 85.64 | 0.00 | 0.78 | 19.97 | 64.90 | 75.77 | | | | | | | 89.9 | 10.1 | 8.24 | 93.9 | 0.65 | 6.1 |
| Rhodococcus erytropolis DSM 1069 | 7.83 | 17.4 | 83.46 | 0.71 | 0.58 | 26.17 | 56.02 | 67.11 | | 100 | 0 | | | | 95.7 | 4.3 | | 93.0 | 0.41 | 7.0 |
| Arthrobacter petroleophagus ATCC 21494 | 7.73 | 15.7 | 70.30 | 3.77 | 0.93 | 9.81 | 55.79 | 79.35 | | 93.3 | 6.7 | | | | 79.0 | 21.0 | 2.31 | 93.8 | 0.97 | 6.2 |
| Rhodococcus sp. DSM 6344 | 7.34 | 22.5 | 70.03 | 0.00 | 0.52 | 15.81 | 53.71 | 76.68 | | | | | | | 93.7 | 6.3 | | 93.1 | 0.59 | 6.9 |
| Aspergillus niger ATCC 9142 | 5.34 | 14.2 | 33.41 | 0.59 | 0.37 | 1.95 | 30.50 | 91.29 | | 93.7 | 6.3 | 82.0 | 18.0 | | 100.0 | 0 | 4.80 | 93.9 | 1.06 | 6.1 |
| Saccharomyces cerivisiae (Canada) | 8.40 | 36.0 | 30.97 | 0.22 | 1.76 | 20.15 | 8.85 | 28.57 | | 91.6 | 8.4 | 86.5 | 13.5 | 2.0 | 91.4 | 8.6 | 2.88 | 96.4 | 0.16 | 3.6 |
| Saccharomyces cerivisiae (Suisse) | 8.22 | 35.0 | 42.71 | 16.90 | 3.28 | 18.11 | 4.42 | 10.34 | | | | 80.6 | 19.4 | 5.2 | 89.2 | 10.8 | 2.13 | 100.0 | 0.23 | 0 |
| Mycobacterium phlei DSM 750 | 7.54 | 23.7 | 81.40 | 64.06 | 14.48 | 2.44 | 0.43 | 0.53 | | 92.8 | 7.2 | 93.6 | 6.4 | 0.4 | 100.0 | 0 | 0.32 | 100.0 | 1.18 | 0 |

EXAMPLE 5

We proceeded according to the general method I described in Example 1, by adding 100 mg of 2-oxo-1-cyclopentanehexanoic acid (obtained by saponification with NaOH of its ethyl ester available from Janssen) to a suspension of *Saccharomyces cerevisiae*. The acid fraction (38.6 mg) of the reaction product was esterified to afford a mixture of esters containing 25% by weight of the methyl ester of the starting acid, as well as the two following compounds:

methyl 2-oxo-1-cyclopentaneacetate (12.9%)
  GC-MS: 156 (41) [M$^+$], 125 (100) [M—OCH$_3^+$], 124 (97), 113 (34), 97 (47), 83 (54) [C$_5$H$_6$O+H$^+$], 74 (48) [M—CH$_2$COOCH$_3^+$], 59 (49)

methyl 2-oxo-1-cyclopentanebutyrate (41.2%)
  GC-MS: 184 (13) [M$^+$], 153 (19) [M—OCH$_3^+$], 152 (53), 137 (18), 124 (28), 101 (4) [M—(CH$_2$)$_3$COOCH$_3^+$], 97 (48), 84 (100) [C$_5$H$_8$O], 74 (47), 55 (38)

I claim:

1. Process for the preparation of cyclic ketones of formula

wherein the dotted line indicates the location of a single or double bond, m represents an integer from 0 to 3 and n an integer from 0 to 10, each of the symbols R, which can be identical or different, stands for hydrogen or for a saturated or unsaturated, linear or branched, hydrocarbon radical having 1 to 6 carbon atoms, and each of the substituent groups can be located in any available position of the ring, which process comprises adding a substrate containing one or several cyclic carboxylic derivatives of formula

wherein the dotted line and the symbols R and m have the meaning indicated in formula (I), p>n+2 and is defined as being an even integer when n is even and an odd number when n is odd, to a culture of a microorganism capable of β-oxidising the fatty acid chain of said derivatives, and contacting said substrate with said culture for an amount of time sufficient to form at least one of said ketones (I) which is then extracted from the reaction medium.

2. Process according to claim 1, which comprises adding a substrate containing one or several derivatives of formula

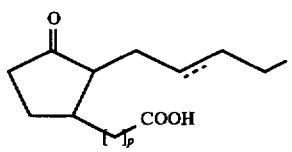

wherein the dotted line indicates the location of a single or double bond and p>n+2 and is odd.

3. Process according to claim 1, which comprises adding a substrate containing one or several derivatives of formula

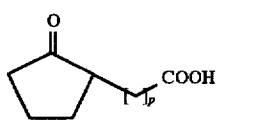

wherein p has the meaning indicated in formula (II).

4. Process according to claim 1, which further comprises selecting the microorganism to be one from the Saccharomyces or Rhodococcus genus.

5. Process according to claim 1, which further comprises selecting the microorganism from the group consisting of *Rhodococcus rhodochorus*, *Rhodococcus erytropolis*, *Rhodococcus sp.*, *Nocardia calcarea*, *Arthrobacter petroleophagus*, *Arthrobacter artrocyanus*, *Arthrobacter ureafaciens*, *Aspergillus niger*, *Saccharomyces cerivisae*, *Mycobacterium phlei*, *Streptomyces viridosporus*, *Streptomyces rosechromogenus*, *Streptomyces bacilliaris*, *Cyclindrocarpon candidum*, *Escherichia coli*, *Hansenula polymorpha*, *Pseudomonas Sp.*, *Serratia marcesens* and *Aspergillus oryzae*.

6. Process according to claim 5, which further comprises adding (Z)-3-oxo-2-(2-pentenyl)-1-cyclopentaneoctanoic acid to a culture of a microorganism selected from the group consisting of *Rhodococcus rhodochorus*, *Rhodococcus erytropolis*, *Rhodococcus sp.*, *Nocardia calcarea* and *Arthrobacter petroleophagus*, to predominantly form (Z)-3-oxo-2-(2-pentenyl)-1-cyclopentaneacetic acid.

7. Process according to claim 5, which further comprises adding 3-oxo-2-pentyl-1-cyclopentaneoctanoic acid to a culture of a microorganism selected from the group consisting of *Serratia marcesens* and *Aspergillus niger*, to predominantly form 3-oxo-2-pentyl-1-cyclopentaneacetic acid.

8. Process according to claim 1, which further comprises subsequently esterifying the formed product to obtain the corresponding ester.

9. Process according to claim 1, wherein the substrate is added to the culture of the microorganism in a medium devoid of any other nutritive source.

* * * * *

UNITED STATES PATENT AND TRADEMARK OFFICE
CERTIFICATE OF CORRECTION

PATENT NO. : 5,667,995

DATED : September 16, 1997

INVENTOR : Whitehead

It is certified that error appears in the above-identified patent and that said Letters Patent is hereby corrected as shown below:

Column 15, line 46: change $>$ to $\geq$.

Column 16, line 8: change $>$ to $\geq$.

Signed and Sealed this

Second Day of December, 1997

*Attest:*

BRUCE LEHMAN

*Attesting Officer*  Commissioner of Patents and Trademarks

UNITED STATES PATENT AND TRADEMARK OFFICE
CERTIFICATE OF CORRECTION

PATENT NO. : 5,667,995

DATED : September 16, 1997

INVENTOR : Whitehead

It is certified that errors appear in the above-identified patent and that said Letters Patent is hereby corrected as shown below:

Column 1, line 33: change "p>n+2" to --p≥n+2--.

Column 2, line 8: change "p>n+2" to --p≥n+2--.

Column 3, line 60: change "*polyrmorpha*" to --*polymorpha*--.

Column 6, line 52: change "Here," to --Hefe,--.

Columns 13 and 14 (TABLE III):

line 2: delete "(−)−"

line 3: delete "trans-A/";

line 4: delete "(+)−"

line 5: change "trans-A" to --(-)-trans-A/(+)-trans-A--.

Signed and Sealed this

Nineteenth Day of May, 1998

*Attest:*

BRUCE LEHMAN

*Attesting Officer*     *Commissioner of Patents and Trademarks*